United States Patent
Bini

(10) Patent No.: US 10,444,333 B2
(45) Date of Patent: Oct. 15, 2019

(54) METHOD AND SYSTEM FOR PERFORMING BASEBAND DIGITAL RECEIVER BEAMFORMING ON ULTRASOUND SIGNALS

(71) Applicant: ESAOTE S.p.A., Genoa (IT)

(72) Inventor: Giovanni Bini, Genoa (IT)

(73) Assignee: ESAOTE S.P.A., Genoa (IT)

( * ) Notice: Subject to any disclaimer, the term of this patent is extended or adjusted under 35 U.S.C. 154(b) by 365 days.

(21) Appl. No.: 15/385,087

(22) Filed: Dec. 20, 2016

(65) Prior Publication Data

US 2017/0184716 A1    Jun. 29, 2017

(30) Foreign Application Priority Data

Dec. 29, 2015    (EP) .................................... 15202989

(51) Int. Cl.
   *G01S 7/52*    (2006.01)
   *A61B 8/00*    (2006.01)
   *G10K 11/34*    (2006.01)

(52) U.S. Cl.
   CPC ........ *G01S 7/52095* (2013.01); *A61B 8/4444* (2013.01); *A61B 8/4483* (2013.01); *G01S 7/52026* (2013.01); *G01S 7/52047* (2013.01); *G10K 11/345* (2013.01); *G10K 11/346* (2013.01); *G01S 7/52092* (2013.01)

(58) Field of Classification Search
   None
   See application file for complete search history.

(56) References Cited

U.S. PATENT DOCUMENTS

| | | | |
|---|---|---|---|
| 5,230,340 A | 7/1993 | Rhyne | |
| 5,349,525 A | * 9/1994 | Dunki-Jacobs | ..... G01S 7/52071 600/437 |
| 5,685,308 A | 11/1997 | Wright | |
| 6,029,116 A | 2/2000 | Wright | |

(Continued)

OTHER PUBLICATIONS

Jieming Ma et al., "Software-Based Ultrasound Phase Rotation Beamforming on Multi-Core DSP," Copyright ® 2011, Texas Instruments Incorporated, 5 pages.

(Continued)

*Primary Examiner* — Brian T Gedeon
(74) *Attorney, Agent, or Firm* — Dickinson Wright PLLC

(57) ABSTRACT

Methods and systems are provided that perform baseband beamforming of ultrasound signals. The methods and systems obtain receive signals from transducers of an ultrasound probe and demodulate the receive signals to obtain complex receive signals having in-phase (I) and quadrature (Q) components. The methods and systems apply time delay and phase correction to the complex receive signals to form delayed complex receive signals before summing the delayed complex receive signals to produce a coherent receive signal. The phase correction includes applying coarse and fine corrections where the coarse correction is calculated as a multiple of a sampling time and the fine correction is calculated as a fraction of the sampling time. The methods and systems apply the coarse and fine corrections contemporaneously by multiplying the complex receive signal by a complex carrier delayed by a multiple of the sampling time and delayed by the fraction of the sampling time.

16 Claims, 9 Drawing Sheets

(56) References Cited

U.S. PATENT DOCUMENTS

| | | | |
|---|---|---|---|
| 6,494,842 B2 * | 12/2002 | Bae | G01S 7/52034 |
| | | | 600/447 |
| 7,583,214 B2 | 9/2009 | Liu et al. | |
| 2006/0074320 A1 | 4/2006 | Yoo et al. | |
| 2007/0229336 A1 | 10/2007 | Liu et al. | |
| 2015/0049578 A1 | 2/2015 | Hoctor et al. | |

OTHER PUBLICATIONS

Anup Agarwal et al., "Image Quality Evaluation with a New Phase Rotation Beamformer," IEEE Transactions on Ultrasonic, Ferroelectrics, and Frequency Control, vol. 55, No. 9, Sep. 2008, pp. 1947-1955.

* cited by examiner

METHOD AND SYSTEM FOR PERFORMING BASEBAND DIGITAL RECEIVER BEAMFORMING ON ULTRASOUND SIGNALS

BACKGROUND OF THE INVENTION

Ultrasound systems exist today that utilize a variety of techniques for processing ultrasound signals to generate information of interest. For example, a variety of techniques exist today for performing beamforming upon ultrasound receive signals. One approach to beamforming performs baseband beamforming upon digitalized receive signals. Baseband digital receiver beamforming with the so-called phase rotation is a technique known in prior art. For example the document U.S. Pat. No. 6,029,116 describes, among other things, such technology.

Digital phase rotation beamforming (PRBF) identified in the technical field of diagnostic, ultrasound imaging has the advantage of allowing the phase difference between signals delayed in different manners and the carrier to be compensated. The demodulating operation provides the multiplication of the carrier by receive signals that, due to the applied delays, are not phase aligned with the carrier.

In the absence of a phase correction, images with focusing defects are obtained due to the fact that the phases of the signal contributions of the individual channels summed with each other are not coherent. One solution suggested in the prior art provides the phase difference of the carrier used in the demodulation to be compensated by performing the reverse process. In substance, the reverse process provides each complex signal contribution to be multiplied by the phase difference of the carrier with the phase of the signal of the reference channel.

However such solution requires a considerable computational burden considering that for a diagnostic image the number of reflection points along only one line and the number of receive lines is very high.

Hardware arrangements have been suggested for dividing the calculation operations between several processors and therefore to perform the calculation operations in parallel. However such solutions depend on the hardware structure of the ultrasound machine that has to be suitable for allowing it to be carried out. When the ultrasound machine has no suitable hardware structures the known arrangements cannot be provided.

SUMMARY

In accordance with embodiments herein, a method is provided for performing baseband beamforming for ultrasound signals. The method comprises obtaining receive signals from transducers of an ultrasound probe; demodulating the receive signals to obtain complex receive signals having in-phase (I) and quadrature (Q) components; applying time delay and phase correction to the complex receive signals to form delayed complex receive signals, the time delay configured to align contributions of reflection signals received by the transducers of the array, the phase correction configured to correct phase differences; and summing, in a coherent manner, the delayed complex receive signals to produce a coherent receive signal focused at a reflection point or a reflection target.

The method is further characterized in that applying time delay includes applying a delay calculated as a multiple of a sampling time and applying the phase correction includes: applying coarse and fine corrections to the signal as time delayed, where the coarse correction is calculated as a multiple of the sampling time; and the fine correction is calculated as a fraction of the sampling time, and wherein the coarse and fine corrections are contemporaneously applied by multiplying the complex receive signal by a complex carrier delayed by a multiple of the sampling time and delayed by the fraction of the sampling time.

The time delay applied to the complex receive signal is based on the coarse correction applied to the complex carrier to achieve a phase correction. In an embodiment such time delay is the same as the coarse correction.

In accordance with embodiments herein, the method further provides, for the signal contribution of each channel, the coarse correction is calculated for each channel as a round function of the time of arrival of a signal component reflected from the reflection point or the target divided by the sampling time. In accordance with embodiments herein, the fine correction is calculated as a difference of a real time of arrival with the coarse correction multiplied by the sampling time, whereby a total delay to be applied for each channel is calculated as the sum of the coarse correction and of the fine correction. In accordance with embodiments herein, the phase correction occurs for each reflection point from which echo signals are derived according to the following equation:

$$PBB(no) = \sum_{bch=0}^{nch-NumCh} Ch(nCh)(n_{(nch)(no)}) * e^{j\omega ddt_{(nCh)(no)}}$$

wherein
nCh=channel number
no=output point
$n_{(nCh)\ (no)}$=input point=round($t_{(nCh)\ (no)}$/sampling time
$dt_{(nCh)\ (no)} = t_{(nCh)\ (no)}$−no*sampling time
$t_{(nCh)\ (no)}$=the calculated position (time) of the input point.

In accordance with embodiments herein, the method further comprises generating sine and cosine values for correction of the carrier and contemporaneously the fine focusing are carried out starting from the same data contained in a table wherein the sampling times are stored and which is used for calculating the coarse delays. In accordance with embodiments herein, the method further comprises providing a parallel multi-line receive (PMR) fine correction in baseband in connection with the individual view lines acquired in parallel contemporaneously with the focusing function. In accordance with embodiments herein, the method further comprises filtering the coherent receive signal with a low-pass filter and downsampling the coherent receive signal to reduce a data-rate and a bandwidth of the coherent receive signal.

In accordance with embodiments herein, an ultrasound system is provided that comprises an input configured to be coupled to an ultrasound probe and receive signals from transducers of the ultrasound probe; a demodulator for demodulating the receive signals to generate complex receive signals by removing the carrier from the receive signal; memory configured to store time delays to align contributions of reflection signals received by the transducers of the array, the memory configured to store phase corrections to correct phase differences introduced by the time delays.

The ultrasound system includes circuitry configured to: apply time delay and phase correction to the complex receive signals to form delayed complex receive signals; and sum, in a coherent manner, the delayed complex receive signals to obtain a coherent receive signal in connection with a reflection point or a reflection target.

The system is characterized in that the memory is configured to store a coarse correction calculated as a multiple of a sampling time, the memory is configured to store a fine correction calculated as a fraction of the sampling time; and the circuitry is configured to apply the coarse and fine corrections contemporaneously by multiplying the complex receive signals by a complex carrier delayed by the multiple of the sampling time and by the fraction of the sampling time.

In accordance with embodiments, the system further comprises a pre-calculated table, stored in the memory. The pre-calculated table comprises real times of arrival of the receive signals relative to a predetermined reflection point. In accordance with embodiments, the system further comprises a processor configured to calculate real times of arrival of the receive signals relative to a predetermined reflection point. In accordance with embodiments, the processor is configured to calculate the coarse delay for baseband signal components of the complex receive signals, in connection with a plurality of channels, by a round function of real times of arrival associated with each of the channels. Optionally, the processor is configured to calculate a fractional value of the fine correction based on real times of arrival for a plurality of channels, the circuit further comprising a complex multiplier configured to multiply the fractional value by the complex receive signal for the corresponding channel to which the corresponding coarse correction has been added.

In accordance with embodiments, the memory is configured to store program instructions and the circuit includes a processor that, when executing the program instructions, is configured to apply the fine and coarse corrections to the complex receive signals. Optionally, the system further comprises a processor configured to provide parallel multiline receive (PMR) fine correction in baseband in connection with individual view lines acquired in parallel contemporaneously with a focusing function.

Embodiments herein relate to a baseband receiver beamforming method for ultrasound signals by means of an ultrasound machine acquiring diagnostic images which ultrasound machine comprises an array of electroacoustic transducers arranged according to a predetermined arrangement and with predetermined relative positions from each other and which transducers are used, alternatively, for generating an excitation ultrasound wave and for receiving the reflection echoes (target) from the tissues under examination. Said reflection echoes generate electric signals corresponding to the received acoustic wave which electric signals are processed by each processing channel and are combined with each other to reconstruct an electric signal that corresponds to the combination of the contributions of the reflection signal of each transducer deriving from a certain reflection target or point, which method comprising the following operations:

subjecting the receive signal of each transducer to an analog/digital conversion;

demodulating the digitized receive signals to eliminate the frequency of the carrier and to center the signal spectrum around value 0 obtaining a complex receive signal with an in-phase component and a quadrature component;

applying to the receive signals of each transducer a time delay corresponding to the difference of the times of arrival of the acoustic signals coming from the reflector point or target to the respective transducer in the array of transducers such to align with each other the contributions of the reflection signals received by the individual transducers of the array and coming from the same reflection point in an iso-phase plane;

applying a phase correction to correct phase differences introduced by the delays applied to the receive signals of the individual transducers;

summing in a coherent manner the delayed signal contributions and with the corresponding phase correction to obtain the receive signal focused on said reflection point or on said reflection target.

Embodiments herein provide improvements to the method allowing the process to be simplified, while keeping the focusing accuracy high and while reducing the computational burden without the need for a specific particular hardware structure.

A further aim of the at least some embodiments herein is to improve the method such to allow delays and phase correction coefficients to be put in table on the basis of general geometrical characteristics of the ultrasound system and particularly of the transducer array.

Still another aim, in accordance with at least some embodiments, is to provide a beamforming processor that allow the method according to the embodiments herein to be carried out.

A further aim is to provide an ultrasound system for acquiring diagnostic images that comprises said beamforming processor.

Embodiments herein achieve the above aims by methods according to what is described above wherein the phase correction provides:

a coarse correction by applying a coarse delay calculated as the multiple of the sampling time;

and a fine correction calculated as the fraction of said sampling time, which corrections are contemporaneously applied by the multiplication by a carrier delayed by the multiple of the sampling time and by a complex carrier of the fraction of the sampling time, obtaining an optimization with fine focusing contemporaneously with the phase correction of the carrier.

Advantageously for the signal contribution of each channel, the coarse phase delay is calculated for each channel as a round function of the time of arrival of the signal component reflected from the reflection point or the target divided by the sampling time, while the fine delay is calculated as the difference of the real time of arrival with the coarse delay multiplied by the sampling time, thereby the total delay to be applied for each channel is calculated as the sum of the coarse delay and the fine delay.

In order to determine the values of coarse delay and fine delay, the method further provides to calculate the real time of arrival of the signal reflection component obtained from a certain reflection point or target.

Further characteristics and improvements of the embodiments herein are the subject matter of the sub-claims.

Embodiments herein relate also to a beamforming processor for carrying out the method described above which beamforming processor comprises:

a plurality of processing channels each one for processing the receive signal of a corresponding transducer;

an analog-digital converter for converting the receive signals of each channel;

a demodulator for extracting from the receive signal of each channel the baseband complex components of the signal by removing the carrier;

an adder for the complex components of the baseband signals to carry out a coherent sum of said components;

there being provided a unit for determining and applying the phase corrections of the carrier with respect to the signal components of the individual channels, which unit comprises:

a calculation unit or a pre-calculated table of the real times of arrival of the receive signal components deriving from a predetermined reflection point;

circuitry configured to:

calculate the coarse delay for the baseband signal components of each channel by a round function of the real time of arrival for each channel;

apply said coarse delay to the baseband signal components for each channel;

determine the fractional value of the delay depending on the real time of arrival for each channel and a complex multiplier of said fractional delay to the complex signal components of each channel to which the corresponding coarse delay has been added;

sum the complex components of all the baseband channels downstream of the complex multiplier.

Embodiments herein relate also to an ultrasound machine provided with said beamforming processor.

BRIEF DESCRIPTION OF THE DRAWINGS

Further improvements and characteristics of the embodiments herein will be clear from the following description of some non-limiting embodiments schematically shown in the annexed figures wherein.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1A:
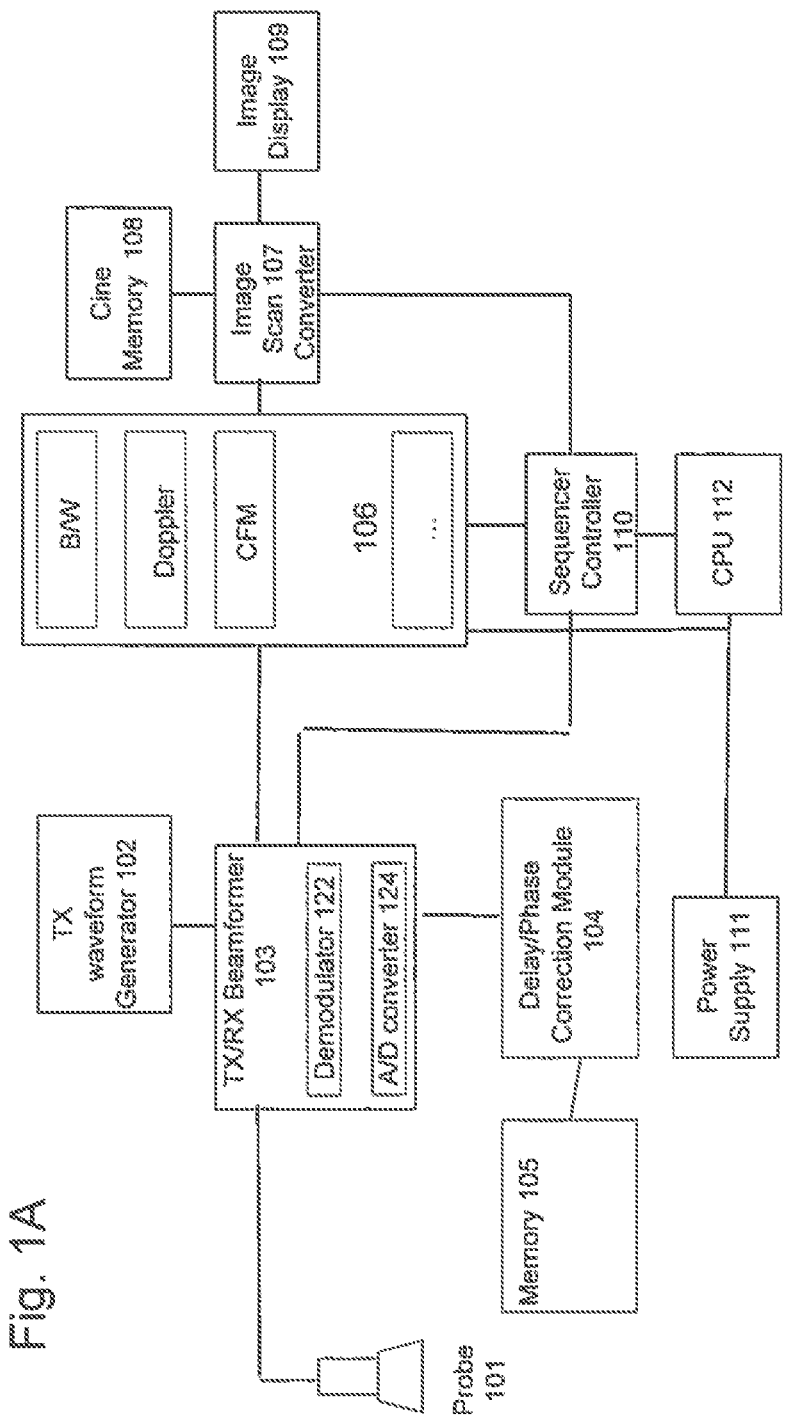
FIG. 1A illustrates a block diagram of an ultrasound system according to an embodiment.

FIG. 1A illustrates a high-level block diagram of an ultrasound system implemented in accordance with embodiments herein. Portions of the system (as defined by various functional blocks) may be implemented with dedicated hardware, analog and/or digital circuitry, and/or one or more processors operating program instructions stored in memory. Additionally or alternatively, all or portions of the system may be implemented utilizing digital components, digital signal processors (DSPs) and/or field programmable gate arrays (FPGAs) and the like. The blocks/modules illustrated in FIG. 1 can be implemented with dedicated hardware (DPSs, FPGAs, memories) and/or in software with one or more processors.

The ultrasound system of FIG. 1 includes one or more ultrasound probes 101. The probe 101 may include various transducer array configurations, such as a one dimensional array, a two dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a beamformer 103. The beamformer 103 includes a transmit (TX) beamformer and a receive (RX) beamformer that are jointly represented by TX/RX beamformer 103. The TX and RX portions of the beamformer may be implemented together or separately. The beamformer 103 supplies transmit signals to the probe 101 and performs beamforming of "echo" receive signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, Doppler imaging, color Doppler imaging, pulse-inversion transmit techniques, contrast-based imaging, M-mode imaging and the like. Additionally or alternatively, the transmit signals may include single or multi-line transmit, shear wave transmit signals and the like.

The beamformer 103 performs beamforming upon received echo signals to form beamformed echo signals in connection pixel locations distributed across the region of interest. For example, in accordance with certain embodiments, the transducer elements generates raw analog receive signals that are supplied to the beamformer. The beamformer adjusts the delays to focus the receive signal along one or more select receive beams and at one or more select depths within the region of interest (ROI). The beamformer adjusts the weighting of the receive signals to obtain a desired apodization and profile. The beamformer applies weights and delays to the receive signals from individual corresponding transducers of the probe. The delayed, weighted receive signals are then summed to form a coherent receive signal.

The beamformer 103 includes (or is coupled to) an A/D converter 124 that digitizes the receive signals at a select sampling rate. The digitization process may be performed before or after the summing operation that produces the coherent receive signals. The beamformer also includes (or is coupled to) a demodulator 122 that demodulates the receive signals to remove the carrier waveform. The demodulation may be performed before or after the summing operation. Once the receive signals are demodulated and digitized, complex receive signals are generated that include I,Q components (also referred to as I,Q data pairs). The I,Q data pairs are saved as image pixels in memory. The I,Q data pairs, defining the image pixels for corresponding individual locations along corresponding lines of sight (LOS) or view lines. A collection of image pixels (e.g., I,Q data pairs) are collected over time and saved as 2D image frames and/or 3D volumes of image data. The image pixels correspond to tissue and other anatomy within the ROI.

Optionally, a dedicated sequencer/timing controller 110 may be programmed to manage acquisition timing which can be generalized as a sequence of firings aimed at select reflection points/targets in the ROI. The sequence controller 110 manages operation of the TX/RX beamformer 103 in connection with transmitting ultrasound beams and measuring image pixels at individual LOS locations along the lines of sight. The sequence controller 110 also manages collection of receive signals.

One or more processors 106 perform various processing operations as described herein.

In accordance with embodiments herein, the beamformer 103 includes an input that configured to be coupled to an ultrasound probe 101 and receive signals from transducers of the ultrasound probe 101. The demodulator 122 demodulates the receive signals to generate complex receive signals by removing the carrier from the receive signal. The memory 105 stores time delays to align contributions of reflection signals received by the transducers of the array of the probe 101. The memory 105 also stores phase corrections to correct phase differences introduced by the time delays.

A delay/phase correction (DPC) module 104 is coupled to the memory 105 and provides various delays and corrections (e.g., coarse, fine, etc.) to the beamformer 103. For example, the DPC module 104 directs the beamformer 103 to apply time delay and phase correction to the complex receive signals to form delayed complex receive signals. The beamformer 103 then sums, in a coherent manner, the delayed complex receive signals to obtain a coherent receive signal in connection with a reflection point or a reflection target.

Optionally, the memory 105 may store coarse corrections calculated as a multiple of a sampling time. A common coarse correction may be stored in connection with multiple channels. Alternatively, different coarse corrections may be stored in connection with various corresponding channels. The memory 105 may also store fine corrections calculated as a fraction of the sampling time. Different fine corrections are be stored in connection with various corresponding channels based on the calculations described herein. As explained herein, the beamformer 103 (circuitry) is configured to apply the coarse and fine corrections contemporaneously by multiplying the complex receive signals by a complex carrier delayed by the multiple of the sampling time and by the fraction of the sampling time.

Optionally, the memory 105 may store a pre-calculated table, where the pre-calculated table comprises real times of arrival of the receive signals relative to a predetermined reflection point. Optionally, the processor 106 may be configured to calculate real times of arrival of the receive signals relative to a predetermined reflection point. Optionally, the processor 106 may be configured to calculate the coarse delay for baseband signal components of the complex receive signals, in connection with a plurality of channels, by a round function of real times of arrival associated with each of the channels. Optionally, the processor 106 may be configured to calculate a fractional value of the fine correction based on real times of arrival for a plurality of channels.

Optionally, the beamformer 103 circuitry may further comprise a complex multiplier configured to multiply the fractional value by the complex receive signal for the corresponding channel to which the corresponding coarse correction has been added.

In accordance with certain embodiments, at least a portion of the beamforming process may be implemented by the processor 106 (e.g., in connection with software based beamforming). For example, the memory 105 may store beamforming related program instructions that are implemented by the processor 106 to apply fine and coarse corrections to the complex receive signals.

Optionally, the processor 106 may be configured to provide parallel multi-line receive (PMR) fine correction in baseband in connection with individual view lines acquired in parallel contemporaneously with a focusing function.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations. Optionally, the processor 106 and/or CPU 112 may filter the first and second displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown.

A control CPU module 112 is configured to perform various tasks such as implementing the user/interface and overall system configuration/control. In case of fully software implementation of the ultrasound signal path, the processing node usually hosts also the functions of the control CPU.

A power supply circuit 111 is provided to supply power to the various circuitry, modules, processors, memory components, and the like. The power supply 111 may be an A.C. power source and/or a battery power source (e.g., in connection with portable operation).

Figure 1B:
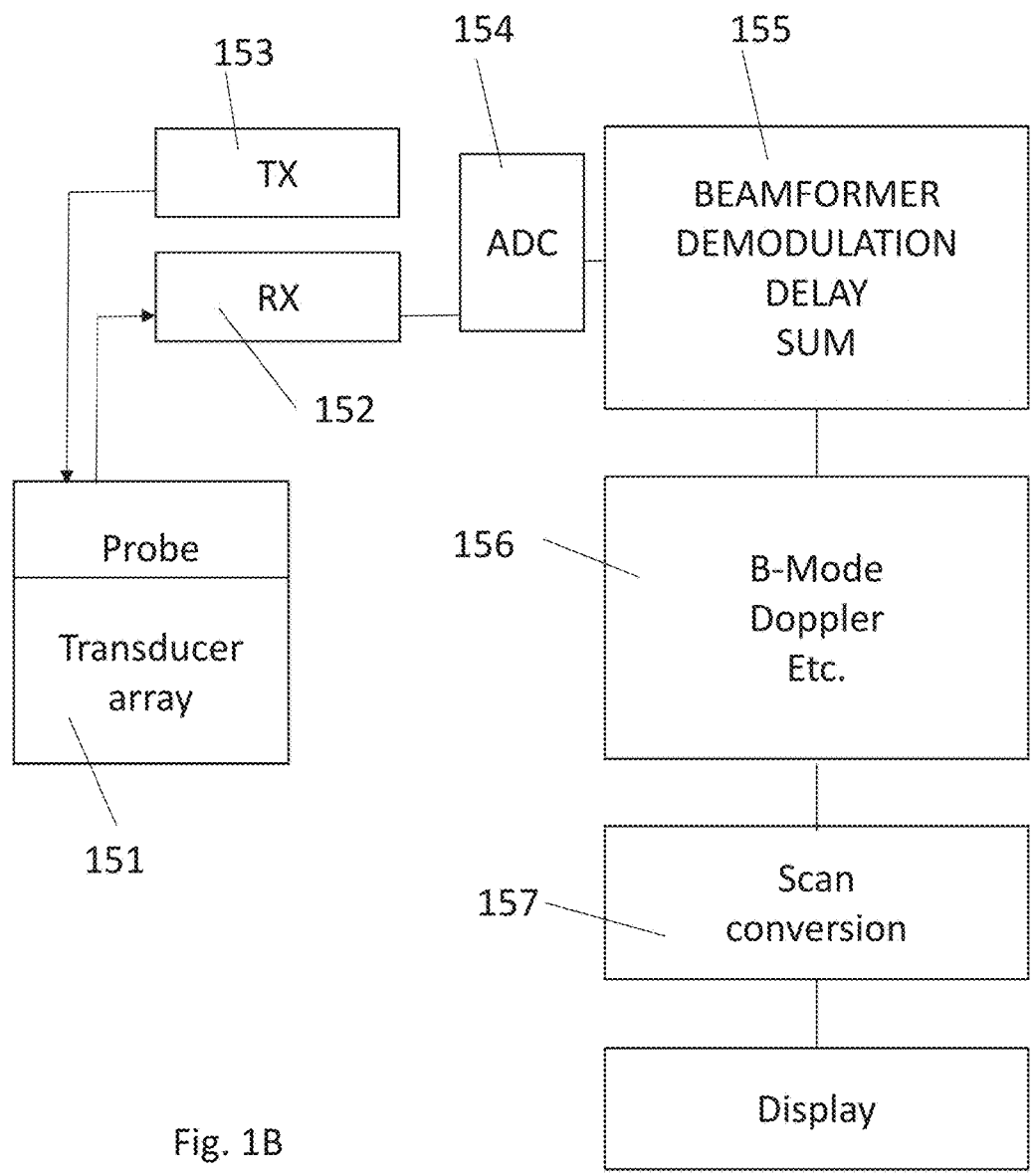
FIG. 1B illustrates a block diagram of an ultrasound system according to an embodiment.

FIG. 1B illustrates a high-level block diagram of an ultrasound system implemented in accordance with embodiments herein. The ultrasound machine for acquiring diagnostic images comprises a probe 151 provided with an array of electroacoustic transducers intended to transform excitation electric signals sent thereto into ultrasound acoustic signals and vice versa the received acoustic signals into corresponding electric signals.

A transmit section and a receive section 152, 153 are connected alternatively one another with the probe to provide to each individual transducer an excitation signal of the corresponding ultrasound pulse and to receive the electric signal corresponding to an acoustic pulse that has hit the transducer.

The receive signals of the transducers are each one sent in an independent manner through a dedicated channel or by a multiplexer to an analog digital converter 154 that samples said signals with a predetermined sampling rate and it provides output digitized receive signals of each transducer/channel.

Therefore digitized signals are subjected to a processing by a so called beamforming processor 155 that carries out the time alignment of the contributions of the receive signal of each channel correspondingly to the travel time of the signal reflected by a predetermined reflection point from said reflection point to the corresponding transducer.

Since the individual transducers of the array provided on the probe have positions different from each other, they necessarily have different distances from the reflection point and therefore the echo signal deriving from such point reaches each individual reflector in a different moment.

The focusing process performs the time re-alignment of the contributions of the receive signal of each transducer deriving from the same reflection point and therefore to sum together such contributions in a coherent manner.

Figure 2:
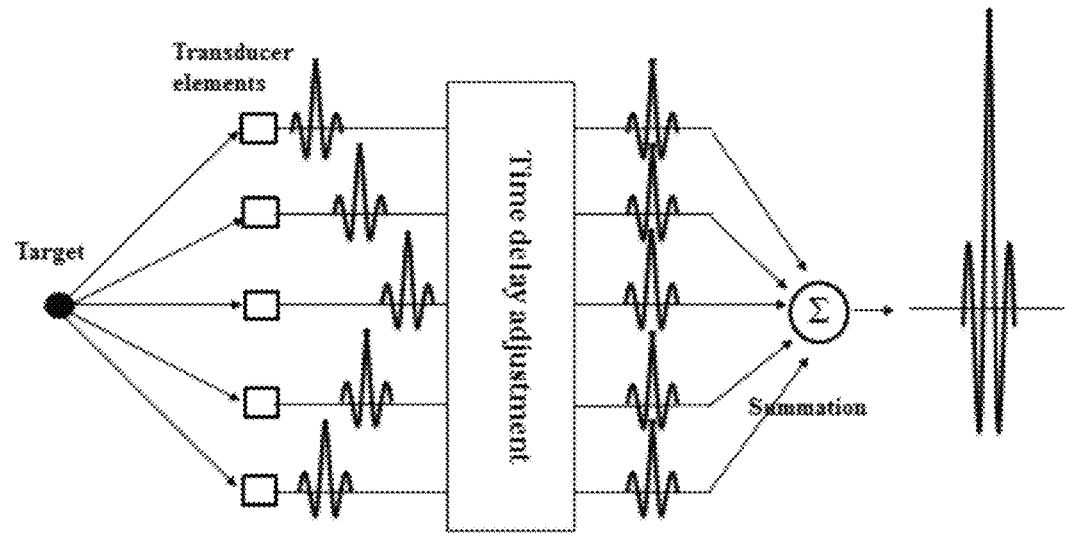
FIG. 2 illustrates a block diagram of a beamforming process in connection with embodiments herein.

FIG. 2 shows an example of such condition.

The process is repeated for each datum along each line forming a two-dimensional or three-dimensional image.

In the baseband beamforming process, the receive signals are subjected to a demodulation for eliminating the carrier, thus obtaining the complex components of the signal that is in-phase components I and quadrature components Q.

The signals obtained by the coherent sum of the time re-aligned contributions of the individual transducers therefore are provided to a processing section 156 for generating images according to different modes such as B mode, Doppler, color Doppler, etc. that then are transmitted to a scan converter 157 in order to be displayed, printed, stored or subjected to other image processing.

Figure 3:
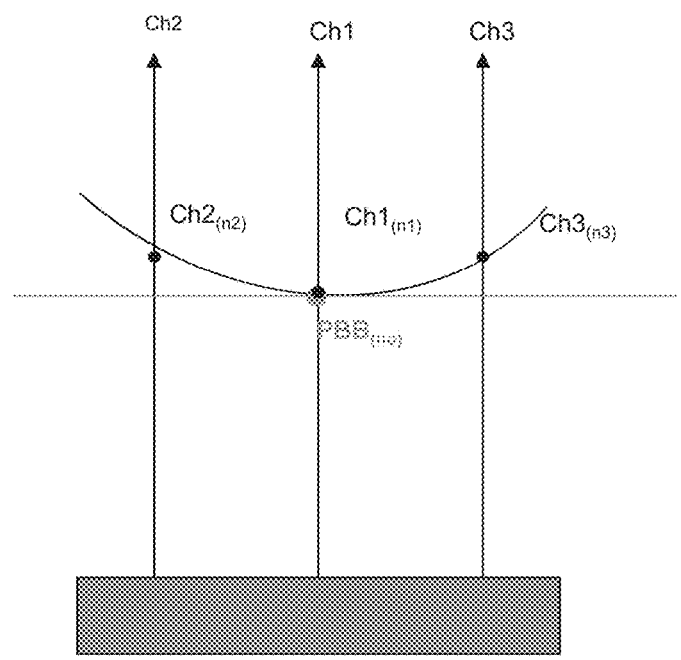
FIG. 3 schematically illustrates an example in which three channels receive an echo signal from the same reflection point.

Considering the simplified example of FIG. 3, wherein the signal received from three channels Ch1, Ch2, Ch3 is shown. The arcuate line shows the propagation front of the receive signal of the same reflector. The points at the intersection between such arcuate line and the straight lines representing the channels are the instants of arrival of the signal to the corresponding transducer n1, n2, n3.

PBBn0 denotes the point with which the contributions of all the channels Ch1, Ch2 Ch3 have to be time aligned in order to be summed in a coherent manner with each other to obtain the receive signal focused on the reflection point in baseband.

The baseband demodulation of the signals Ch(n) can be described by the equation:

$$ChBB_{(n)} = Ch_{(n)} e^{-j\omega d n St}$$

Wherein:

$ChBB_{(n)}$ = the signal of the channel $Ch_{(n)}$ related to the transducer n in the transducer array and ωd = the carrier frequency n = the number of the channel, i.e. of the transducer St = the sampling time by means of which the receive signal has been converted from analog to digital.

The focused signal PBB(n) therefore is described by the following relation:

$$PBB(n) = ChBB1(n1) + ChBB2(n2) + ChBB3(n3)$$

Namely it is composed of the coherent sum of the baseband contributions of the receive signals of the individual channels and corresponding transducers.

Therefore in detail:

$$PBB(n) = Ch1(n1)\ e^{-j\omega d n1 St}\ +Ch2(n2)\ e^{-j\omega d n2 St}\ +Ch3(n3)$$
$$e^{-j\omega d n3 St}$$

Therefore it is immediately clear that due to the different time delays between the individual channels, the receive signals of such channels are multiplied by carriers having phases different from each other, therefore it is not possible to obtain a good focusing.

Therefore in order to perform a baseband beamforming it is required to perform a phase shift of the carrier before the coherent sum step.

Such phase shift is described by the following equation:

$$PBB(n0) = CBB1(n1)\ e^{j\omega d(n1-n0)St}\ +CBB2(n2)\ e^{j\omega d(n2-n0)St}\ +CBB3(n3)$$
$$e^{j\omega d(n3-n0)St}$$

n1−n0, n2−n0 and n3−no means a coarse delay calculated as the difference between the carrier at point Ch1($n1$), Ch2($n2$), Ch3($n3$) and the carrier at the reference point with zero delay.

This coarse delay represents an integer multiple of the sampling time.

On the contrary the fine delay is a value equal to a fraction of the sampling time.

By considering the following definitions:

n = index of the transducer or channel the receive signal is calculated for;

t1, t2, t3 real values of the sampling time that is the real delay time from the instant of acquisition of the three channels.

Application of the coarse delay:
n1 = round(t1/sampling time)
n2 = round(t2/sampling time)
n3 = round(t3/sampling time).

Carrier Compensation:
dc1 = ($n$1−$n$0)*sampling time
dc2 = ($n$2−$n$0)*sampling time
dc3 = ($n$3−$n$0)*sampling time.

Fine Delay:
df1 = t1−($n$1\*sampling time)
df2 = t2−($n$2\*sampling time)
df3 = t3−($n$3\*sampling time)

Total Delay:
dt1 = dc1+df1 = t1−n0\*sampling time.
dt2 = dc2+df2 = t2−n0\*sampling time.
dt3 = dc3+df3 = t3−n0\*sampling time.

Therefore by the above definitions we have:

$$PBB(n0) = Ch1(n1) * e^{j\omega d\ dt1} + Ch2(n2) * e^{j\omega d\ dt2} + Ch3(n3) * e^{j\omega d\ dt3}$$

By generalizing the example of FIG. 3 to which the equations listed above refer and by expressing them in a generic manner for the focusing on any point, we have the following equation:

$$PBB_{(no)} = \sum_{nch=0}^{NumCh} Ch(nch)(n_{(nch)(no)}) \cdot e^{j\omega d dt_{(nch)(no)}}$$

wherein
$PBB_{(no)}$ = the focused output data;
no = output point index;
nch = channel index;
NumCh = total number of channels;
Ch(1 ... NumCh, 1 ... NumPoints) = the whole array of acquired data;

NumPoints=total number of acquired points for a single channel;

$n_{(nch)\,(no)}$=input sample for channel nch for designated output point index no=round($t_{(nch)\,(no)}$/sampling time);

wd=2p*demodulation frequency;

$dt_{(nch)\,(no)}=t_{(nch)\,(no)}$–no*sampling time, i.e. the delay applied to the designated input sample;

$t_{(nch)\,(no)}$=the calculated acquisition time for designated input sample.

By defining $FocVal_{(nch)\,(no)}=t_{(nch)\,(no)}$/Sampling time–no

It is possible to obtain values of $dt_{(nch)\,(no)}$ and $n_{(nch)\,(no)}$ also at hardware level by using the following formulas:

$$dt_{(nch)(n)}=FocVal_{(nch)(n)}*Sampling\ time$$

$$n_{(nch)(no)}=round(FocVal_{(nch)(n)})+no$$

and wherein $dt_{(nch)\,(n)}$ is the total delay including both the coarse delay and the fine delay and $n_{(nch)\,(n)}$ is the coarse delay.

From the above it is easy to understand that the coarse delay is the integer value of the time of arrival of the signal to the corresponding transducer, while the fine delay is about the decimal values of such time.

What pointed out above highlights the advantage of the method according to the embodiments herein by means of which it is possible to optimize the focusing of complex baseband signals I/Q by a fine focusing obtained contemporaneously with the carrier phase correction.

Figure 4:
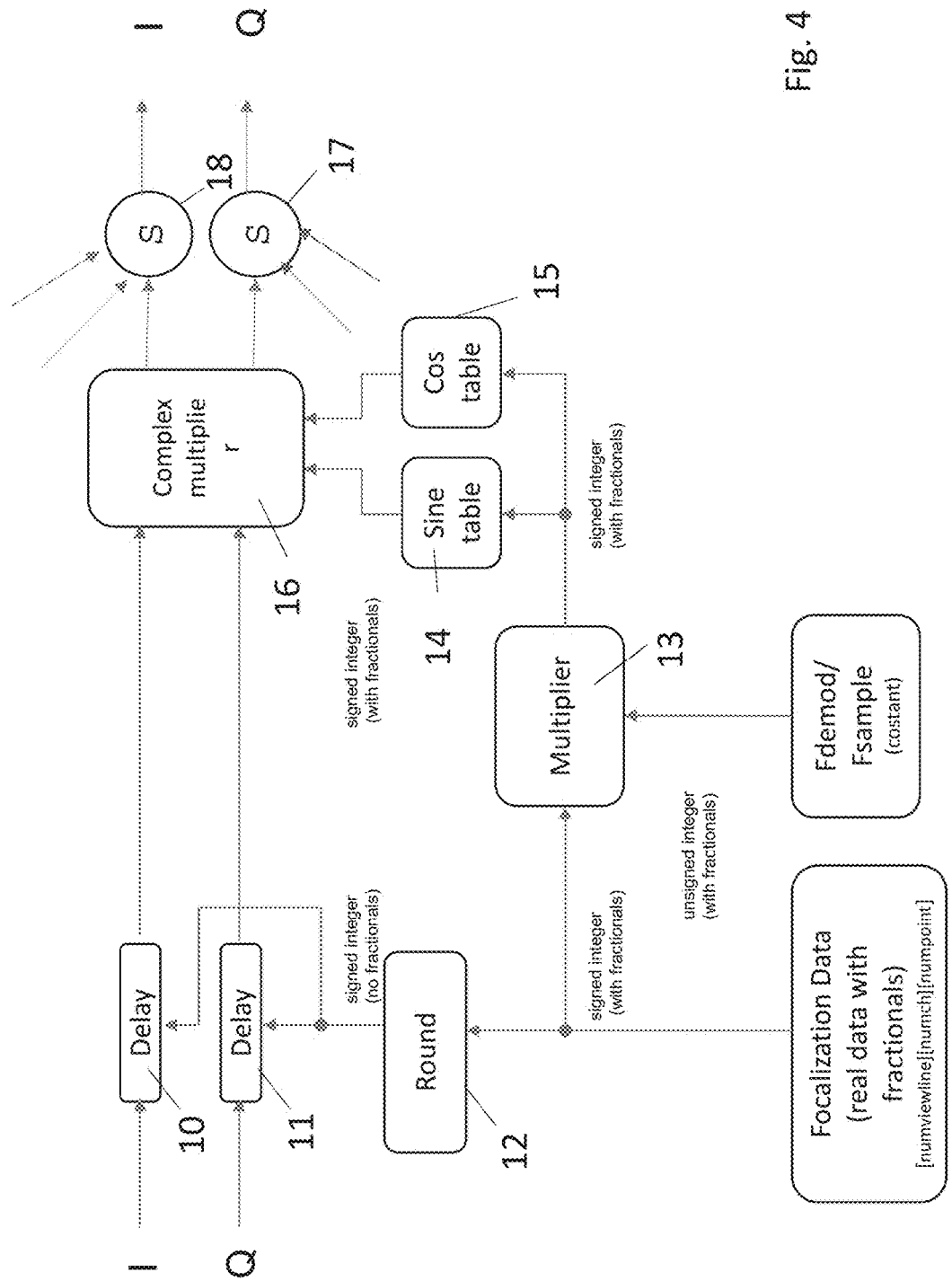
FIG. 4 illustrates a block diagram of a beamformer formed in accordance with embodiments herein.
Figure 5:
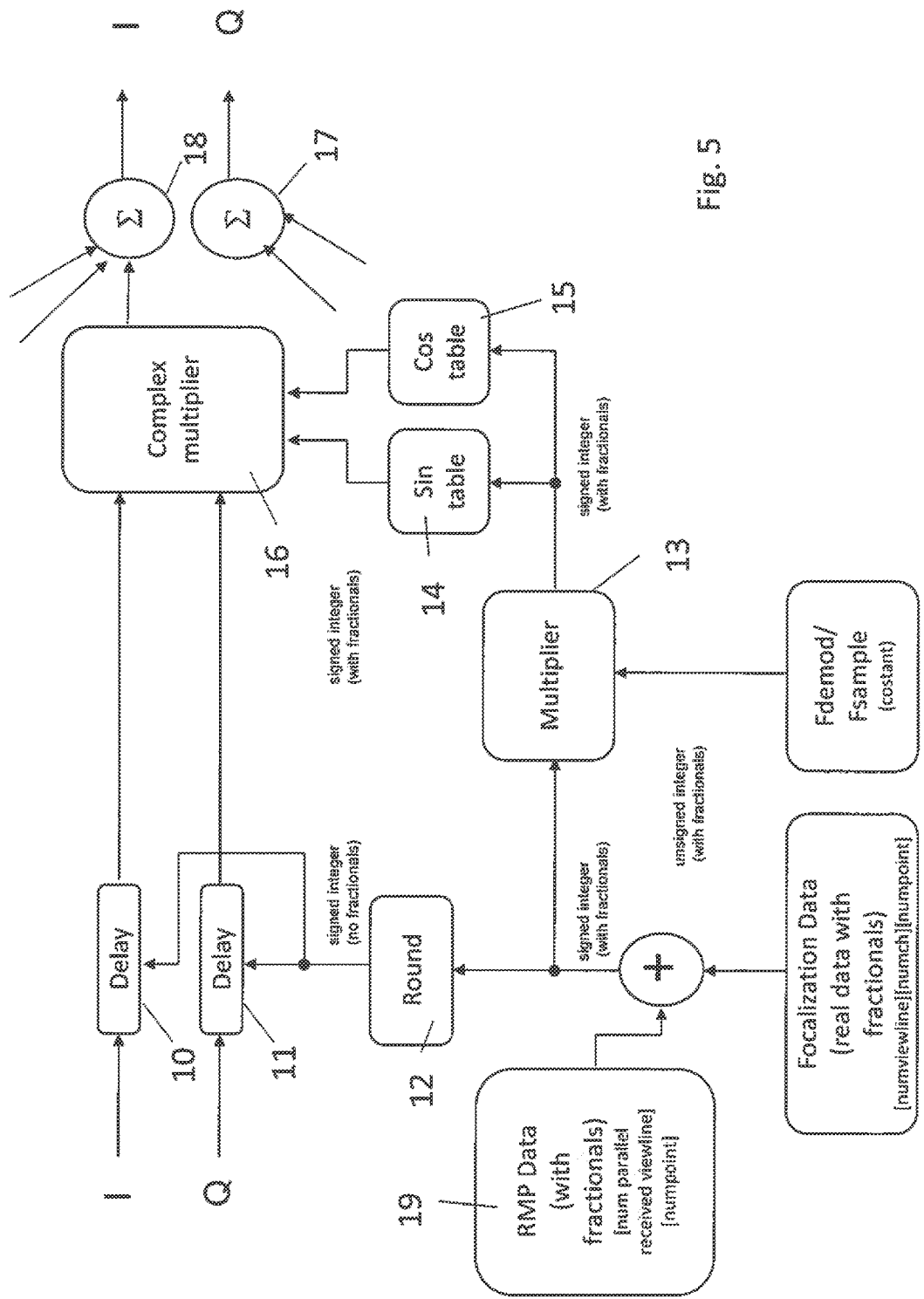
FIG. 5 illustrates a block diagram of a beamformer formed in accordance with embodiments herein.
Figure 6:
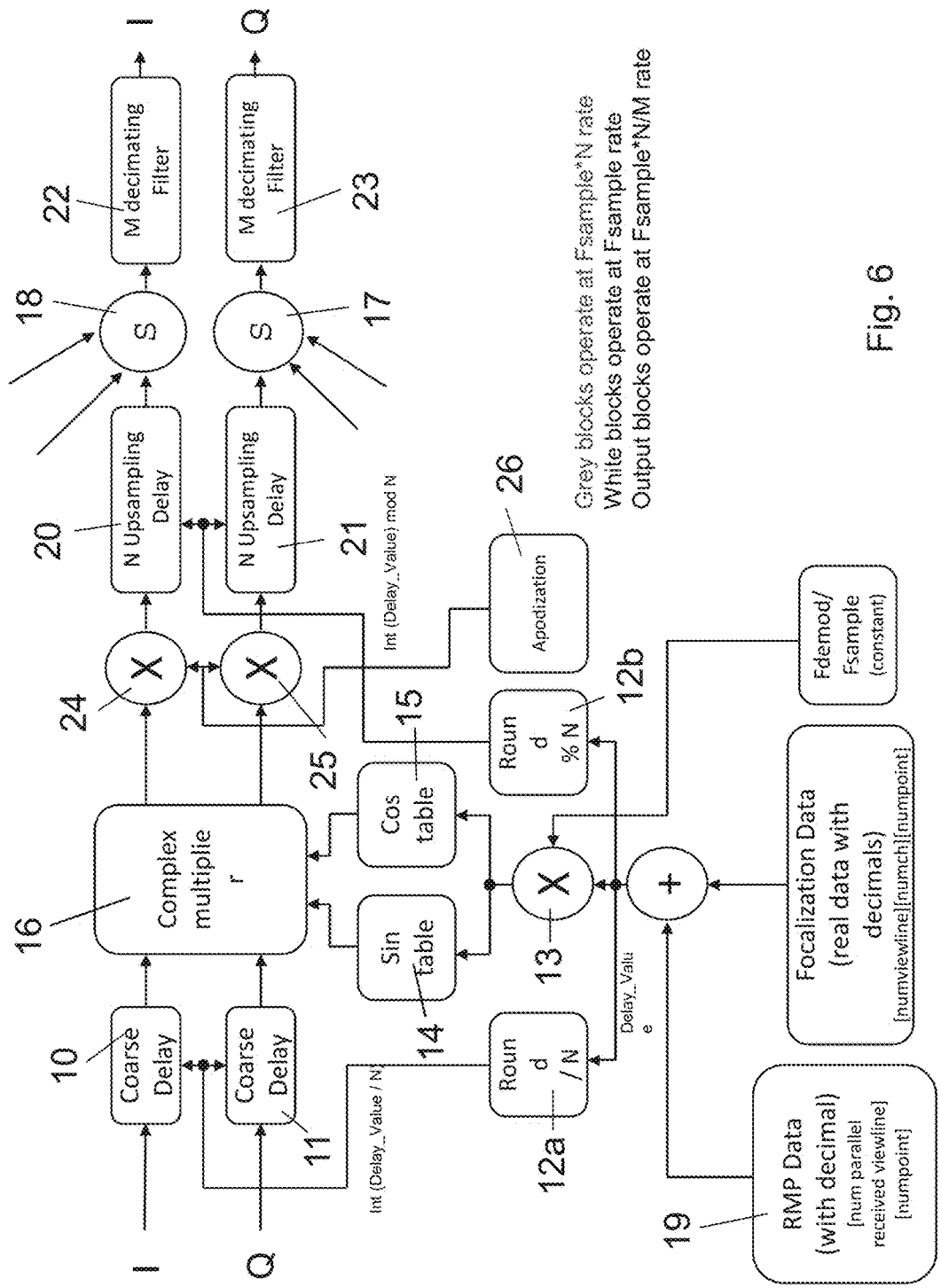
FIG. 6 illustrates a block diagram of a beamformer formed in accordance with embodiments herein.

With reference to FIGS. 4 to 6 they show the block diagrams of three different embodiments of a beamforming processor according to the embodiments herein.

As it will be clear from the three block diagrams, a common and advantageous feature is the fact that the generation of sine and cosine values is provided for carrier correction and contemporaneously fine focusing starting from the same data contained in the table used for calculating the coarse delays.

FIG. 5 further provides a combination of the method according to the embodiments herein with a Parallel Multi-line Receive algorithm (RMP) in baseband with fine correction of the individual view lines acquired in parallel contemporaneously with the focusing function.

In particular FIG. 4 shows a functional block diagram of a beamforming processor according to the embodiments herein.

The signals received by the individual transducers demodulated for extracting the I and Q baseband signal components for each channel, are subjected to the application of the delays in modules 10 and 11. The applied delay is determined according to what described above by the integer part of the real value (integer and decimals) of the sampling time. To such extent, at 12 the round function is applied to such real value obtaining for the respective channel and transducer, that is for the corresponding signal, the coarse delay n(nch)(no)=round(FocVal(nch)(n)).

The multiplier 13 generates the phase rotation value for the fine focusing and phase correction as defined by the formula $$Phase=FocVal\ (nch)(n)*SampleTime*fDemod$$

Therefore such value is transformed by a table of sine and cosine values 14 and 15 which values are used for applying the fine focusing correction in the complex multiplier 16. I and Q signal components processed in this manner for each channel are then summed at 17 and 18 obtaining the receive signal focused on the corresponding reflection point from which the echoes processed by the beamforming processor come.

Phase correction is achieved by using the coarse delay also in the phase rotation as seen above.

It is clear how by determining the sampling time it is possible to obtain both the coarse delay for the carrier phase correction, and the one for the fine focusing and how such values can be easily calculated beforehand and put in tables.

FIG. 5 is different from the processor according to the preceding embodiment for the fact that a functional block 19 has been added which performs the RMP optimization function (Parallel Multi-line reception) in baseband with fine correction of the individual view lines acquired in parallel contemporaneously with the focusing function.

In such FIG. 5 the identical functional blocks or having identical functions as in FIG. 4 have the same identification number.

The RMP algorithm adds a data set for each view line and for each point acquired in parallel. The algorithm allows each focused point to be moved in order to align the received lines for each transmission compensating for the eventual no flat propagation wavefront of transmission.

The algorithm of FIG. 6 provides a different configuration. The identical functional blocks or having identical functions as in FIGS. 4 and 5 have the same reference numbers.

In the beamforming processor according to such functional block diagram, to which a functionality of oversampling by a factor N has been added, the focusing data are calculated at the sampling rate Fsample multiplied by N. This in order to further improve the accuracy in the focusing (both coarse and fine) by a factor N since the accuracy of coarse and fine delays increases by such value N.

The fine focusing is applied like what described in FIGS. 4 and 5 by the blocks 13, 14, 15, 16 while the coarse delay block (10, 11) uses the integer part of the delays calculated according to the formula "Integer part of the delay value"/N (block 12a). The added blocks of the medium-coarse delays (20,21) use a delay value calculated as "Integer part of the delay value" modulus % N (block 12b).

The blocks 10,11,12a,12b,13,14,15,16,19 operate at the Fsample rate.

Blocks 17,18 are the only to operate at Fsample×N rate.

Blocks 20 and 21 operate at the Fsample rate but generate output data at Fsample×N rate. The functionality of blocks 20 and 21 can be obtained by different hardware types, such as by way of example and not as a limitation: polyphase filters, shift register, multiplexer, summations.

Blocks 22, 23 can be implemented by low-pass filters of the Fir type with integrated decimation function that receive input data at the Fsample×N rate but calculate the output data at Fsample×N/M rate.

It is clear that by selecting the suitable values for the factors N and M as well as the cutoff frequency of the filters present in blocks 22 and 23 it is always possible to focus the data with a suitable resolution (Fsample×N) as well as to have output data with the band suitably reduced at (Fsample×N/M) rate. Moreover the fine focusing blocks 12, 13, 14, 15, 16, 19 operate at a multiple resolution of Fsample×N allowing for a more accurate focusing.

Therefore:

In 13, 14, 15,16 the fine delays comprehensive of the fractional part are applied likewise the diagram of FIGS. 4 and 5 but with a resolution increased by a factor N.

In 10 and 11 the coarse delays generated by the round function and divided by the oversample factor are applied.

In 20 and 21 the medium-coarse delays calculated as "Integer part of the delay value" modulus N (the remaining of the division) are applied. After the coherent sum of the signals a downsampling by a factor M (not necessarily equal to N) and a filtering by a low-pass filter 22, 23 are performed on I and Q signals.

The oversampling functionality described above can be advantageously used with any type of beamforming in the time domain, both in baseband and radiofrequency.

In this implementation, to improve beamforming performances, the optional blocks 24,25 and 26 may be added to introduce an apodization feature that allow each channel to be weighted by an appropriate coefficient.

Figure 7:
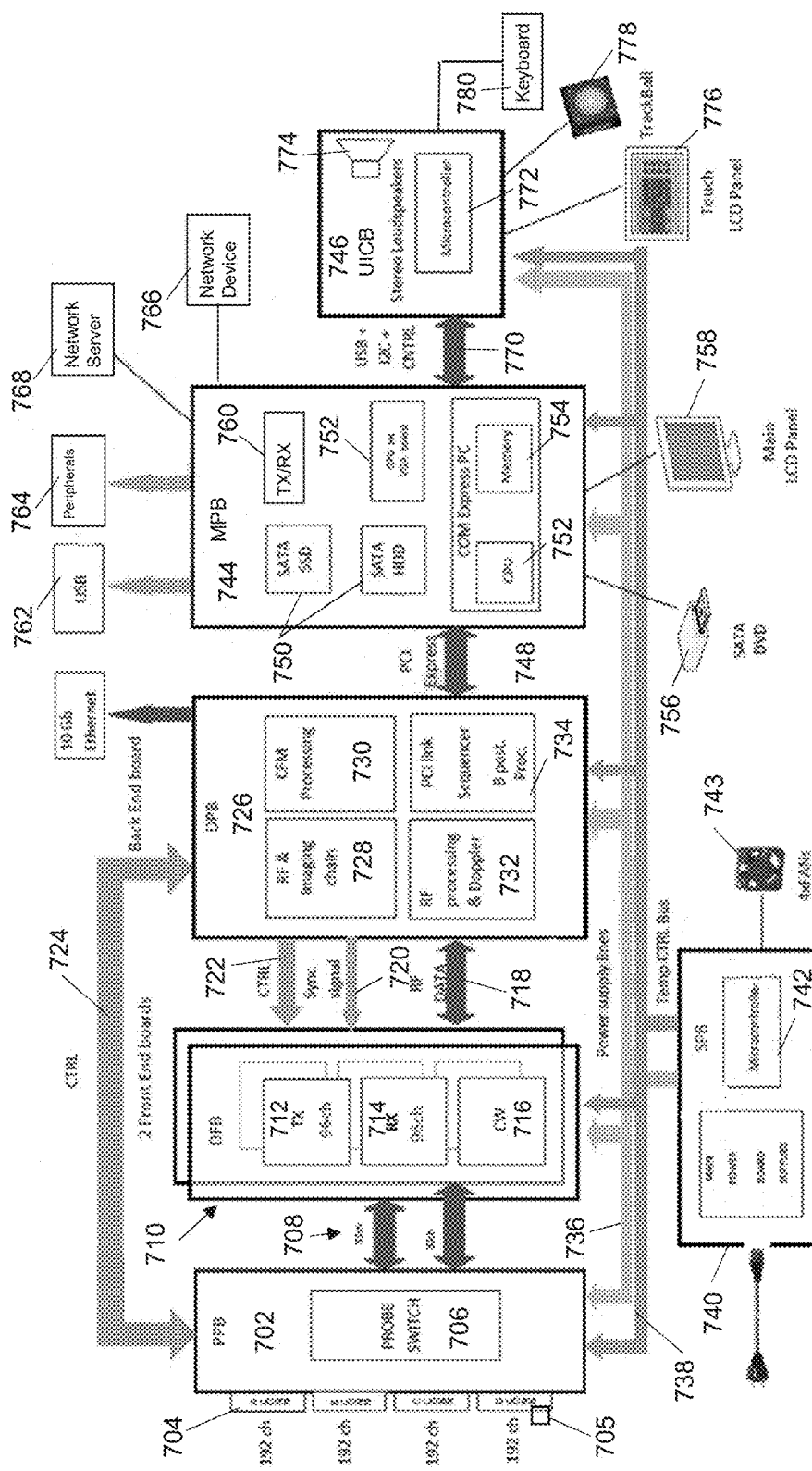
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a select one of the connection ports 704. The connect signal may be generated by the probe when power is initially supplied to the probe when coupled to the connection port 704. Additionally or alternatively, each connection port 704 may include a sensor 705 that detects when a mating connection on a cable of a probe has been interconnected with the corresponding connection port 704. The sensor 705 provides be ca connect signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front end boards 710 may convert the RF ultrasound data to I,Q data pairs which are then passed to the digital processing board 726.

The digital processing board 726 includes an RF and imaging module 728, a color flow processing module 730, an RF processing and Doppler module 732 and a PCI link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
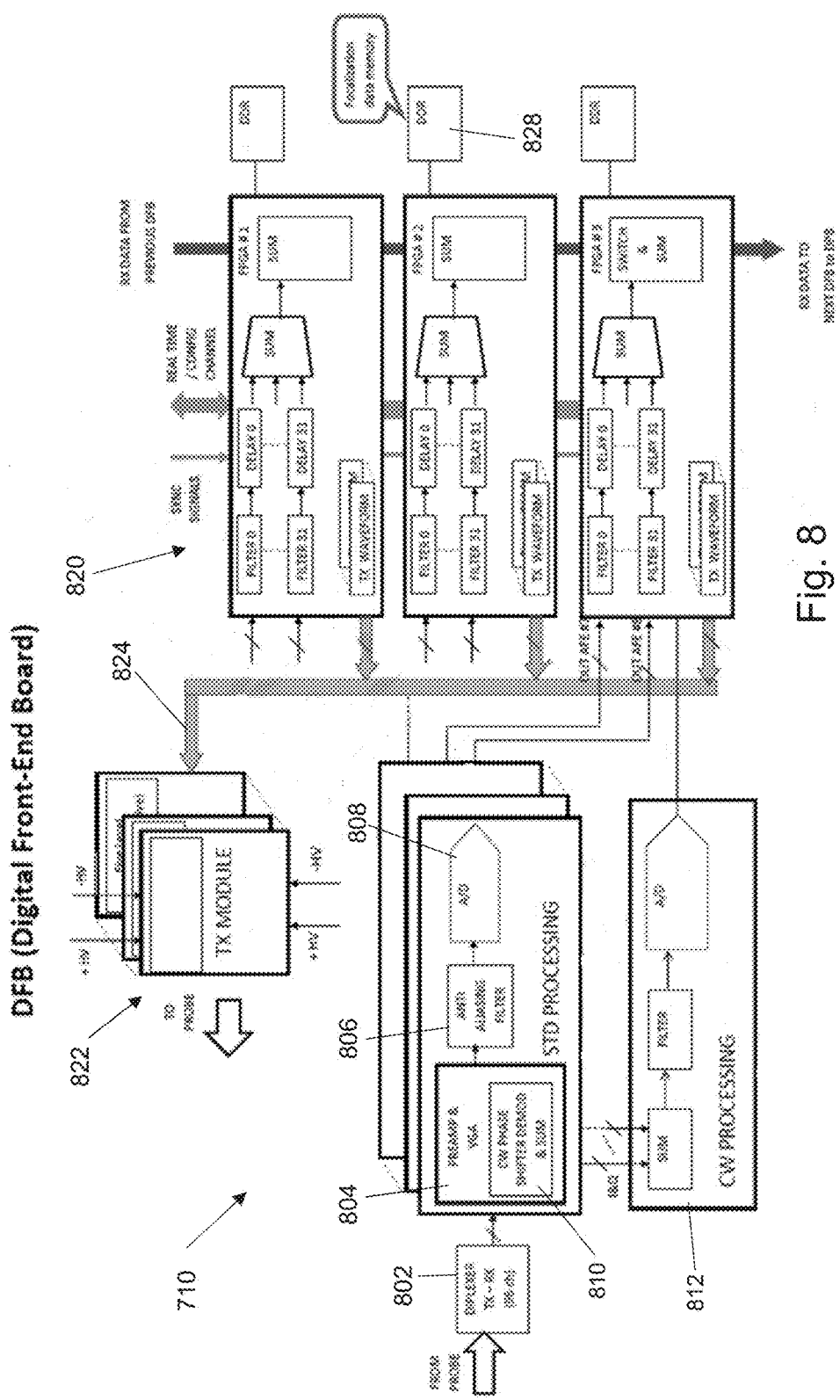
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering. The output thereof is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The being formed RF data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
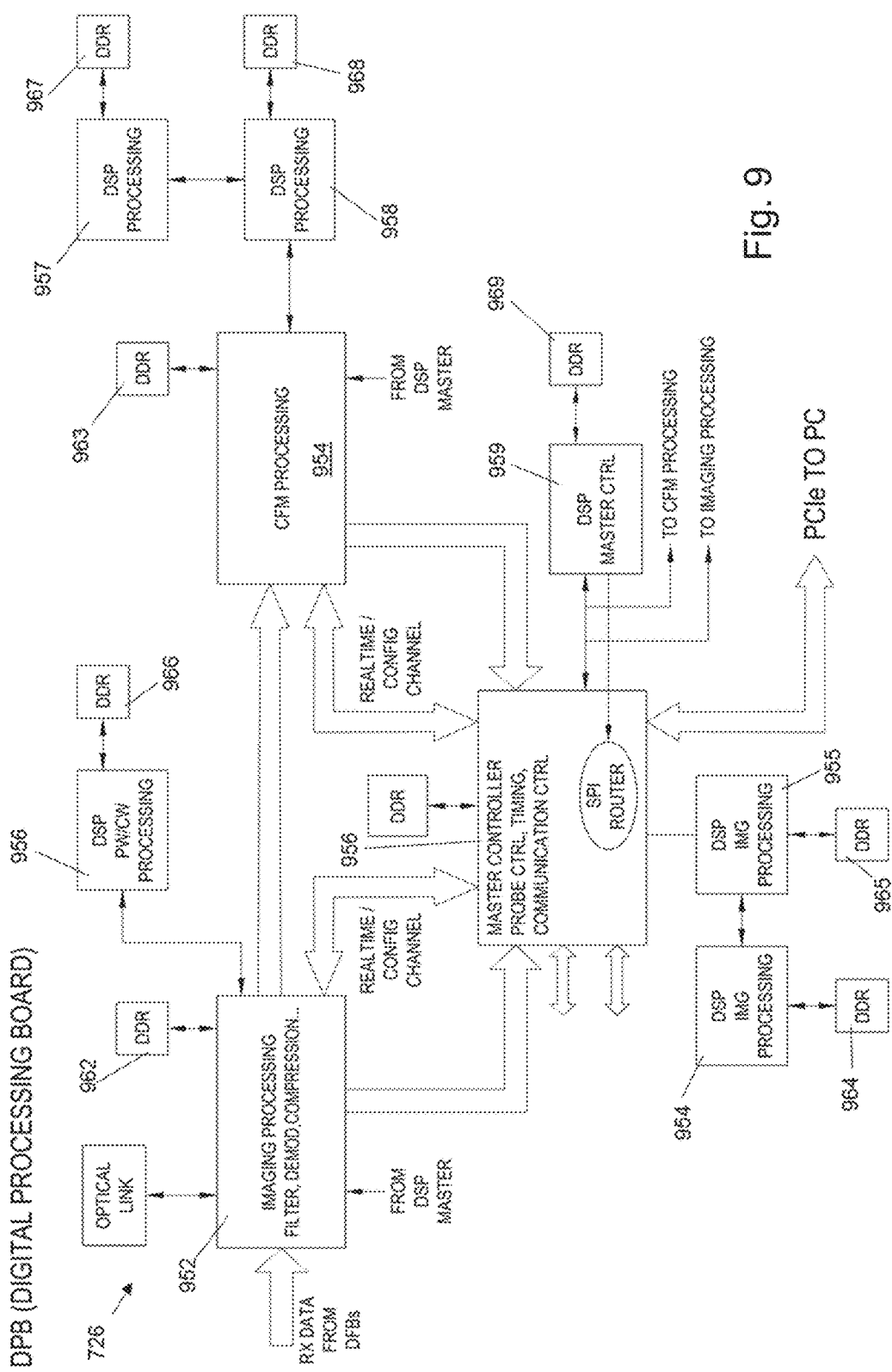
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 950 provides real-time configuration information and synchronization signals in connection with each channel to the digital front-end board 710.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming.

The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for performing baseband beamforming for ultrasound signals, the method comprising:
   obtaining receive signals from transducers of an ultrasound probe;
   demodulating the receive signals to obtain complex receive signals having in-phase (I) and quadrature (Q) components;
   calculating a coarse correction as a multiple of a sampling time;
   calculating a fine correction as a fraction of the sampling time;
   applying time delay and phase correction to the complex receive signals to form delayed complex receive signals; and
   summing, in a coherent manner, the delayed complex receive signals to produce a coherent receive signal focused at a reflection point or a reflection target,
   wherein
   applying time delay includes delaying the complex receive signal by the course correction;
   applying the phase correction includes:
      multiplying the complex receive signal by a complex carrier delayed by the coarse correction and the fine correction.

2. The method according to claim 1, wherein for the signal contribution of each channel, the coarse correction is calculated for each channel as a round function of the time of arrival of a signal component reflected from the reflection point or the target divided by the sampling time.

3. The method according to claim 2, wherein the fine correction is calculated as a difference of a real time of arrival with the coarse correction multiplied by the sampling time, whereby a total delay to be applied for each channel is calculated as the sum of the coarse correction and of the fine correction.

4. The method according to claim 1, wherein the phase correction occurs for each reflection point from which echo signals are derived according to the following equation:

$$PBB_{(no)} = \sum_{nch=0}^{NumCh} Ch(nch)(n_{(nch)(no)}) \cdot e^{jwddt_{(nch)(no)}}$$

wherein
$PBB_{(no)}$=the focused output data;
no=output point index;
nch=channel index;
NumCh=total number of channels;
Ch(1 . . . NumCh, 1 . . . NumPoints)=the whole array of acquired data;
NumPoints=total number of acquired points for a single channel;
$n_{(nch)(no)}$=input sample for channel nch for designated output point index no=round($t_{(nch)(no)}$/sampling time);
wd=$2\pi$*demodulation frequency;
$dt_{(nch)(no)}=t_{(nch)(no)}$–no*sampling time, i.e. the delay applied to the designated input sample;
$t_{(nch)(no)}$=the calculated acquisition time for designated input sample.

5. The method according to claim 1, further comprising generating sine and cosine values for correction of the carrier based on fine and coarse delays contained in a table wherein the sampling times are stored.

6. The method according to claim 1, further comprising providing a parallel multi-line receive (PMR) fine correction in baseband in connection with the individual view lines acquired in parallel contemporaneously with the focusing function.

7. The method according to claim 1, further comprising filtering the coherent receive signal with a low-pass filter and downsampling the coherent receive signal to reduce a data-rate and a bandwidth of the coherent receive signal.

8. An ultrasound system, comprising:
   an input configured to be coupled to an ultrasound probe and receive signals from transducers of the ultrasound probe;
   a demodulator for demodulating the receive signals to generate complex receive signals by removing the carrier from the receive signal;
   memory configured to store time delays and phase corrections;
   circuitry configured to:
      apply time delay and phase correction to the complex receive signals to form delayed complex receive signals; and
      sum, in a coherent manner, the delayed complex receive signals to obtain a coherent receive signal in connection with a reflection point or a reflection target;
   wherein
      the memory is configured to store a coarse correction calculated as a multiple of a sampling time;
      the memory is configured to store a fine correction calculated as a fraction of the sampling time; and
      the circuitry is configured to:
         delay the complex receive signals by the coarse correction;
         apply the phase correction by multiplying the delayed complex receive signals by a complex carrier delayed by the coarse correction and the fine correction.

9. The system according to claim 8, wherein the circuitry comprises one or more processors that, when executing program instructions, are configured to perform at least one of the apply or sum operations.

10. The system according to claim 8, further comprising a processor configured to calculate real times of arrival of the receive signals relative to a predetermined reflection point.

11. The system according to claim 10, wherein the processor is configured to calculate the coarse delay for baseband signal components of the complex receive signals, in connection with a plurality of channels, by a round function of real times of arrival associated with each of the channels.

12. The system according to claim 10, wherein the processor is configured to calculate a fractional value as the fine correction based on real times of arrival for a plurality of channels, the circuit further comprising a complex multiplier configured to multiply the fractional value by the complex receive signal for the corresponding channel to which the corresponding coarse correction has been added.

13. The system according to claim 8, wherein the memory is configured to store program instructions and the circuit includes a processor that, when executing the program instructions, is configured to apply the fine and coarse corrections to the complex receive signals.

14. The system according to claim 8, further comprising a processor configured to provide parallel multi-line receive (PMR) fine correction in baseband in connection with individual view lines acquired in parallel contemporaneously with a focusing function.

15. The system according to claim 8, further comprising a pre-calculated table, stored in the memory, the pre-calculated table comprising real times of arrival of the receive signals relative to a predetermined reflection point.

16. A method for performing baseband beamforming for ultrasound signals, the method comprising:

obtaining receive signals from transducers of an ultrasound probe;

demodulating the receive signals to obtain complex receive signals having in-phase (I) and quadrature (Q) components;

applying time delay and phase correction to the complex receive signals to form delayed complex receive signals; and summing, in a coherent manner, the delayed complex receive signals to produce a coherent receive signal focused at a reflection point or a reflection target, wherein applying time delay includes applying a delay calculated as a multiple of a sampling time;

applying the phase correction includes:

applying coarse and fine corrections to the signal as time delayed;

the coarse correction calculated as a multiple of the sampling time; and the fine correction calculated as a fraction of the sampling time, wherein the coarse and fine corrections are contemporaneously applied by multiplying the complex receive signal by a complex carrier delayed by a multiple of the sampling time and delayed by the fraction of the sampling time;

the time delay applied to the complex receive signal is based on the coarse correction applied to the complex carrier; and for the signal contribution of each channel, the coarse correction is calculated for each channel as a round function of the time of arrival of a signal component reflected from the reflection point or the target divided by the sampling time.

* * * * *